(12) United States Patent
Ohara et al.

(10) Patent No.: US 10,548,466 B2
(45) Date of Patent: Feb. 4, 2020

(54) LIGHT SOURCE MODULE AND ENDOSCOPE LIGHT SOURCE SYSTEM

(71) Applicant: OLYMPUS CORPORATION, Tokyo (JP)

(72) Inventors: Satoshi Ohara, Hachioji (JP); Eiji Yamamoto, Hachioji (JP); Takeshi Ito, Hino (JP); Masahiro Nishio, Hachioji (JP); Hiroyuki Kamee, Koganei (JP); Motoki Tabata, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 458 days.

(21) Appl. No.: 15/215,717

(22) Filed: Jul. 21, 2016

(65) Prior Publication Data

US 2016/0324408 A1 Nov. 10, 2016

Related U.S. Application Data

(63) Continuation of application No. PCT/JP2015/051214, filed on Jan. 19, 2015.

(30) Foreign Application Priority Data

Jan. 23, 2014 (JP) .................................. 2014-010727

(51) Int. Cl.
*A61B 1/06* (2006.01)
*A61B 1/07* (2006.01)
(Continued)

(52) U.S. Cl.
CPC ........ *A61B 1/0669* (2013.01); *A61B 1/00006* (2013.01); *A61B 1/00105* (2013.01);
(Continued)

(58) Field of Classification Search
CPC ... A61B 1/0669; A61B 1/00126; A61B 1/002; A61B 1/0646; A61B 1/07;
(Continued)

(56) References Cited

U.S. PATENT DOCUMENTS 5,749,830 A * 5/1998 Kaneko .............. A61B 1/00082
348/E5.038
5,800,343 A * 9/1998 Takeuchi ................. A61B 1/07
600/132

(Continued)

FOREIGN PATENT DOCUMENTS

CN 101485558 A 7/2009
JP H04-070710 A 3/1992
(Continued)

OTHER PUBLICATIONS

English machine translation of JP 2006-181061A (Year: 2006).*
(Continued)

*Primary Examiner* — Alexandra L Newton
*Assistant Examiner* — Genja M Frankert
(74) *Attorney, Agent, or Firm* — Scully, Scott, Murphy & Presser, P.C.

(57) ABSTRACT

A first light source module includes a light source-side connection hole to which a irradiation-side connector of a irradiation module is mechanically detachably attached. The light source-side connection hole is made common to the first irradiation-side connector, which is mounted in the first irradiation module, and the second irradiation-side connector, which is mounted in the second irradiation module, such that the light source-side connection hole is connectable to the first irradiation-side connector and the second irradiation-side connector.

22 Claims, 8 Drawing Sheets

(51) Int. Cl.
*G02B 23/24* (2006.01)
*A61B 1/00* (2006.01)
*H04N 5/225* (2006.01)
*A61B 1/002* (2006.01)

(52) U.S. Cl.
CPC ............ *A61B 1/063* (2013.01); *A61B 1/0646* (2013.01); *A61B 1/07* (2013.01); *G02B 23/2469* (2013.01); *H04N 5/2256* (2013.01); *A61B 1/002* (2013.01); *A61B 1/00126* (2013.01); *A61B 1/0684* (2013.01); *H04N 2005/2255* (2013.01)

(58) Field of Classification Search
CPC .. A61B 1/00105; A61B 1/06; G02B 23/2461; G02B 23/26; H04N 5/2256; H04N 2005/2255
See application file for complete search history.

(56) References Cited

U.S. PATENT DOCUMENTS

| | | | |
|---|---|---|---|
| 6,371,908 B1 | | 4/2002 | Furusawa et al. |
| 6,374,025 B1* | | 4/2002 | Iriyama .................... G02B 6/32 385/116 |
| 2002/0089586 A1 | | 7/2002 | Suzuki et al. |
| 2010/0080016 A1* | | 4/2010 | Fukui .................... A61B 1/0653 362/574 |

FOREIGN PATENT DOCUMENTS

| JP | H09-292575 A | 11/1997 |
|---|---|---|
| JP | 2000-23903 A | 1/2000 |
| JP | 2002-112962 A | 4/2002 |
| JP | 2003-164417 A | 6/2003 |
| JP | 2006-181061 A | 7/2006 |
| JP | 2006181061 A * | 7/2006 |
| JP | 2006-204341 A | 8/2006 |
| JP | 2009-072213 A | 4/2009 |
| JP | 2010-042153 A | 2/2010 |
| JP | 2012-010962 A | 1/2012 |
| JP | 2013-125608 A | 6/2013 |

OTHER PUBLICATIONS

Chinese Office Action dated Jan. 30, 2019 in Chinese Patent Application No. 201580005256.4.
International Search Report dated Apr. 14, 2015 issued in PCT/JP2015/051214.
Japanese Office Action dated Feb. 20, 2018 in Japanese Patent Application No. 2014-010727.
Extended Supplementary European Search Report dated Oct. 18, 2017 in European Patent Application No. 15 74 0283.5.
English translation of the International Preliminary Report on Patentability together with the Written Opinion dated Aug. 4, 2016 received in related International Application No. PCT/JP2015/051214.
Chinese Office Action dated Jun. 13, 2018 in Chinese Patent Application No. 201580005256.4.
Japanese Office Action dated Aug. 1, 2017 in Japanese Patent Application No. 2014-010727.
Chinese Office Action dated Jul. 25, 2017 in Chinese Patent Application No. 201580005256.4.

* cited by examiner

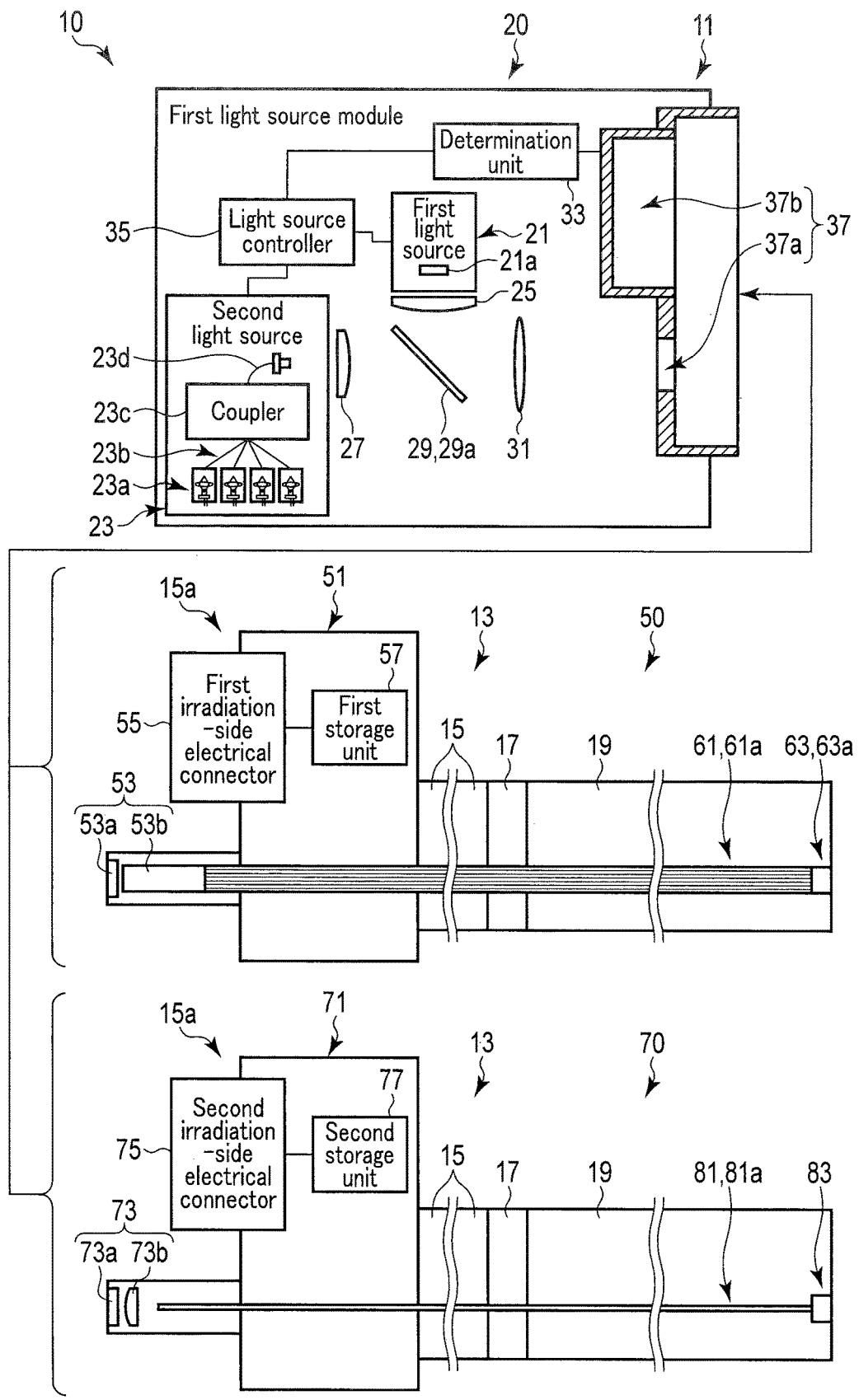
F I G. 1

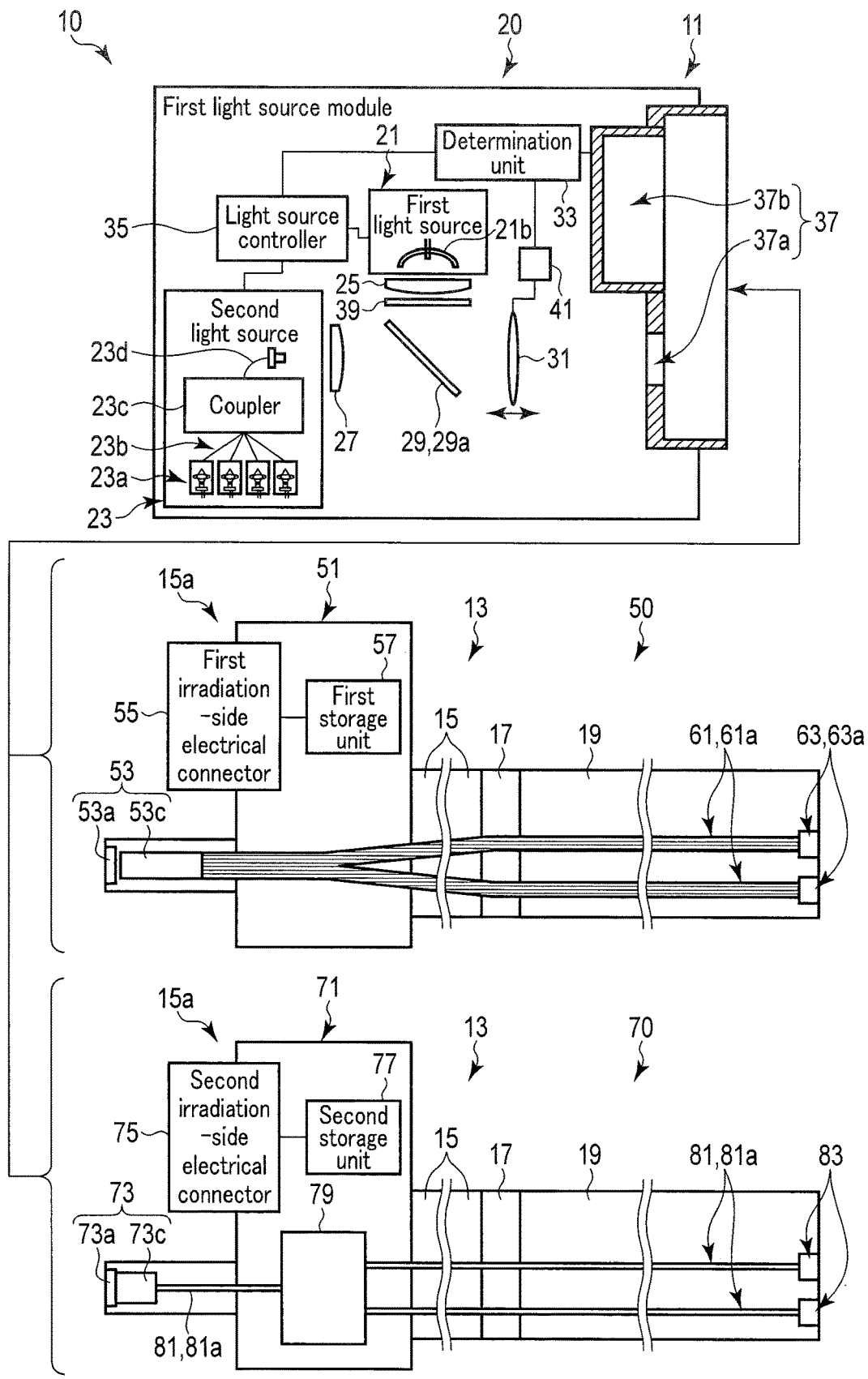
F I G. 5

LIGHT SOURCE MODULE AND ENDOSCOPE LIGHT SOURCE SYSTEM

CROSS-REFERENCE TO RELATED APPLICATIONS

This application is a Continuation Application of PCT Application No. PCT/JP2015/051214, filed Jan. 19, 2015 and based upon and claiming the benefit of priority from prior Japanese Patent Application No. 2014-010727, filed Jan. 23, 2014, the entire contents of all of which are incorporated herein by reference.

BACKGROUND OF THE INVENTION

1. Field of the Invention

The present invention relates to a light source module, and an endoscope light source system including the light source module.

2. Description of the Related Art

For example, Jpn. Pat. Appln. KOKAI Publication No. 2013-125608 discloses an example of a light source system in which a plurality of light sources and light guide members corresponding to the respective light sources are mounted. In this light source system, three kinds of light sources, namely a laser light source, a lamp light source and an LED light source, are combined with a single optical fiber for laser light, and a bundle fiber for lamp light and LED light.

In addition, in this light source system, selective use is implemented in accordance with a purpose of use, such that the lamp light source or LED light source is used for white-light illumination for use in normal optical observation, and the laser light source is used for narrow-band illumination for use in special optical observation.

BRIEF SUMMARY OF THE INVENTION

According to one embodiment of the invention, there is provided a light source module including a light source-side connection hole to which a irradiation-side connector of a irradiation module is mechanically detachably attached, such that illumination light corresponding to a purpose of use is emitted from the irradiation module by a combination of the light source module and the irradiation module. The light source-side connection hole is made common to a first irradiation-side connector, which is mounted in a first irradiation module, and a second irradiation-side connector, which is mounted in a second irradiation module, such that the light source-side connection hole is connectable to the first irradiation-side connector and the second irradiation-side connector.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic view of a first light source module according to a first embodiment of the present invention, and an endoscope light source system including the first light source module.

FIG. 5 is a schematic view of a first light source module according to a second embodiment, and an endoscope light source system including the first light source module.

DETAILED DESCRIPTION OF THE INVENTION

Hereinafter, embodiments of the present invention will be described in detail with reference to the accompanying drawings. Incidentally, in some drawings, depiction of some of members is omitted for the purpose of clearer illustration.

First Embodiment

[Structure]

A first embodiment will be described with reference to FIG. 1, FIG. 2, FIG. 3A and FIG. 3B.

[Structure of Endoscope Light Source System 10]

Figure 3A:
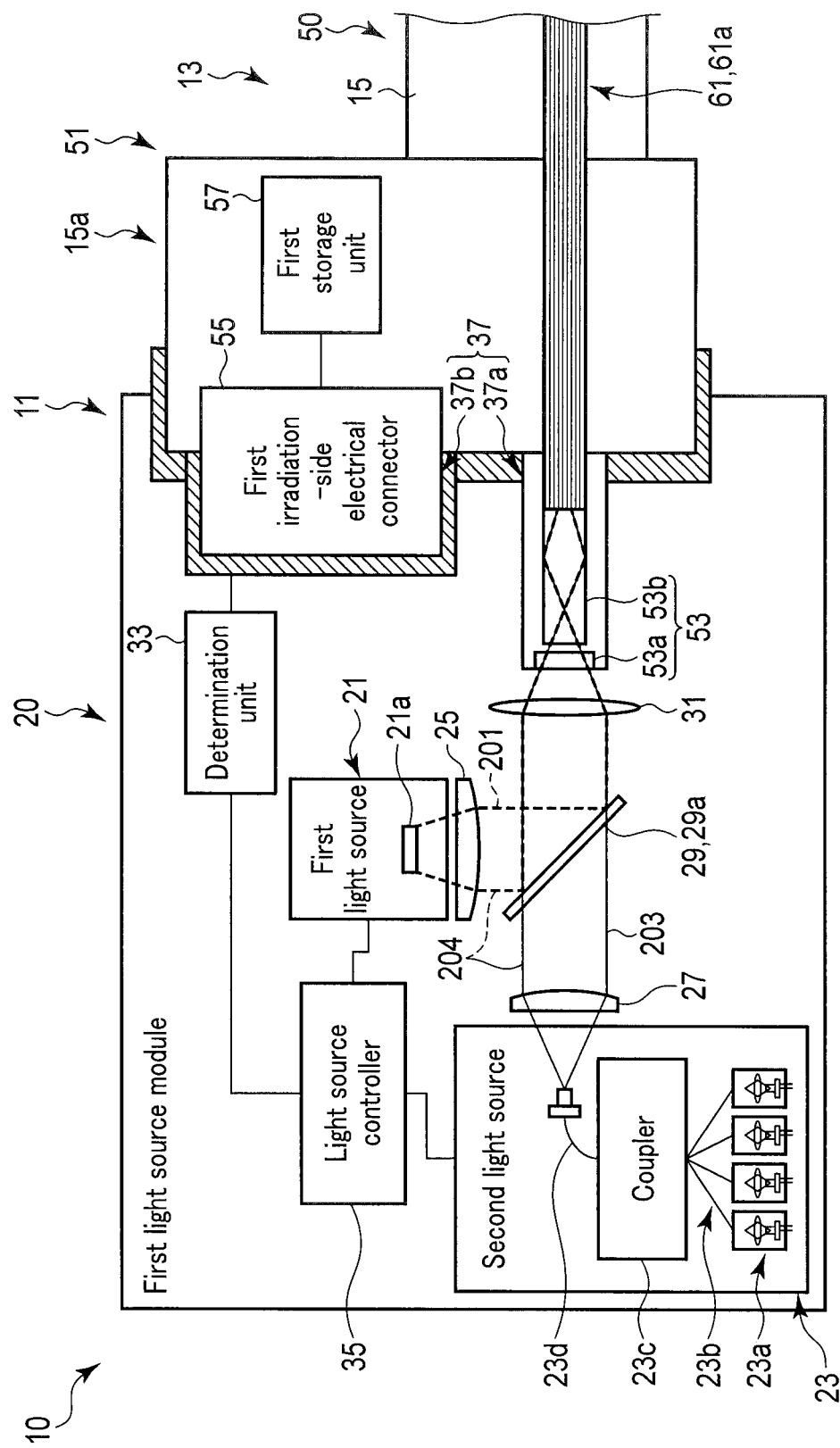
FIG. 3A is a view illustrating a state in which the first light source module shown in FIG. 1 is connected to a first irradiation module.
Figure 3B:
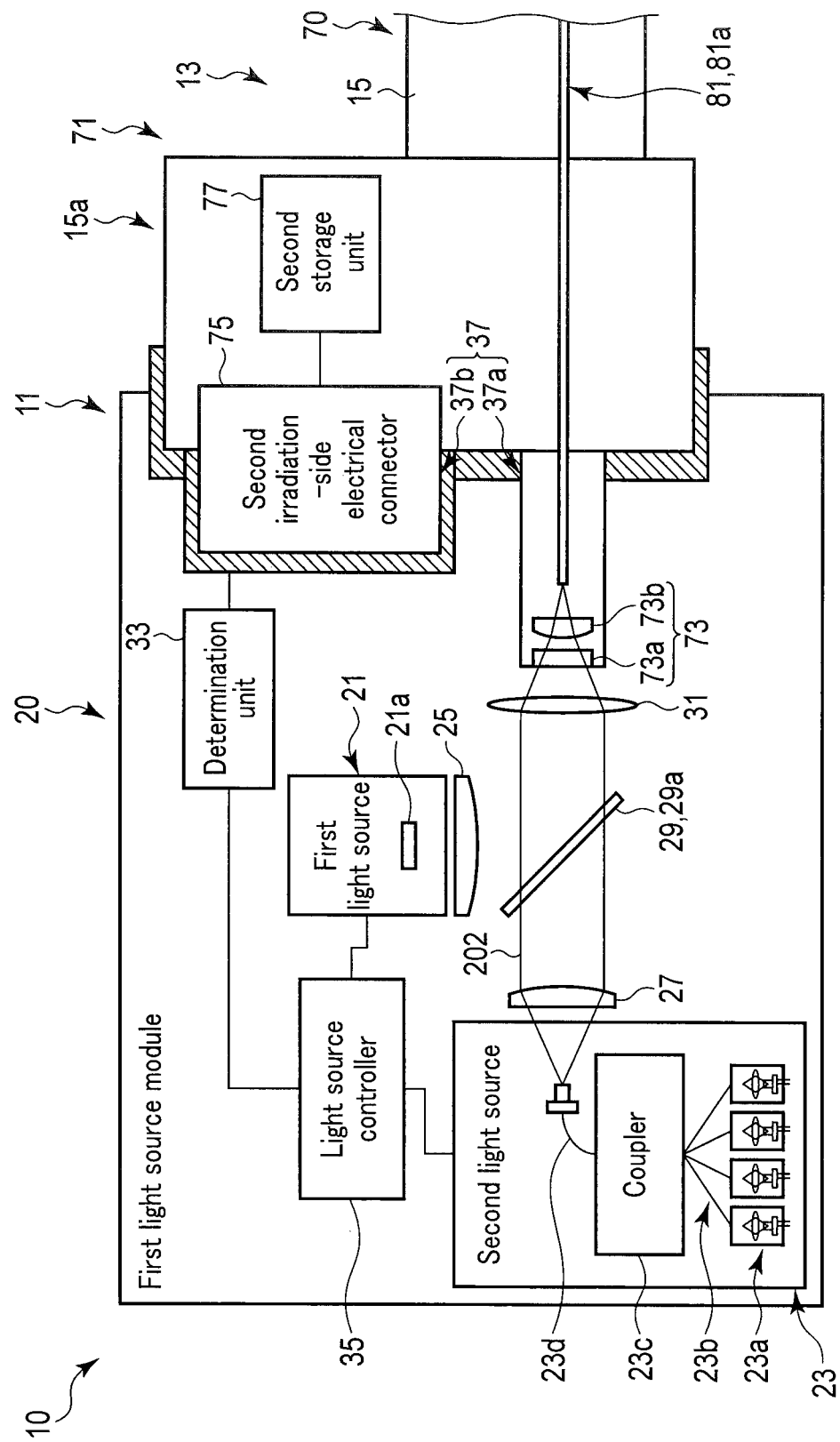
FIG. 3B is a view illustrating a state in which the first light source module shown in FIG. 1 is connected to a second irradiation module.

An endoscope light source system 10 as illustrated in FIG. 1 includes a light source module, and an irradiation module which can be mechanically detachably attached to the light source module. As illustrated in FIG. 1, the endoscope light source system 10 is composed of, for example, one light source module (first light source module 20) and two irradiation modules (first irradiation module 50 and second irradiation module 70). The respective irradiation modules 50 and 70 are various kinds of modules having, for example, mutually different optical characteristics. In addition, as illustrated in FIG. 1, FIG. 3A and FIG. 3B, the first light module 20 and the irradiation module 50, 70 are combined such that when the first irradiation module 50 is attached to the first light source module 20, the second irradiation module 70 is detached from the first light source module 20, and such that when the second irradiation module 70 is attached to the first light source module 20, the first irradiation module 50 is detached from the first light source module 20. By this combination, illumination light corresponding to a purpose of use is emitted from the irradiation module 50, 70, which is connected to the first light source module 20. Furthermore, the first light source module 20 is a common member which is shared and made common to the first irradiation module 50 and second irradiation module 70.

The first light source module 20 is mounted on, for example, a light source device 11, and the irradiation module

50, 70 is mounted on, for example, an endoscope 13 which is detachably attached to the light source device 11.

[Light Source Module]

Hereinafter, referring to FIG. 1, FIG. 3A and FIG. 3B, a description is given of a concrete structure of the light source module by taking the first light source module 20 as an example.

As illustrated in FIG. 1, FIG. 3A and FIG. 3B, in the first light source module 20, a first light source 21, and a second light source 23 with a light emission area, which is smaller than a light emission area of the first light source 21, are mounted. The first light source 21 includes an LED light source 21a which emits LED light that is first light, and the second light source 23 includes a laser light source 23a which emits a laser beam that is second light. The first light source 21 and second light source 23 are disposed such that the optical axis of the first light emitted from the first light source 21 and the optical axis of the second light emitted from the second light source 23 cross perpendicular to each other.

Depending on purposes of use, there are many combinations of the LED light source 21a and laser light source 23a. Hereinafter, a description is given of, for example, a case in which the LED light source 21a is used for normal optical observation, and the laser light source 23a is used for special optical observation. In the meantime, the special optical observation refers to, for example, observation for distinguishing a superficial vessel and a deep vessel in a living body.

The LED light source 21a includes a white LED which emits white LED light. The laser light source 23a includes a LD which emits a laser beam with a wavelength of 405 nm, a LD which emits a laser beam with a wavelength of 445 nm, and a LD which emits a laser beam with a wavelength of 515 nm.

The second light source 23 includes single light guide members 23b on which laser beams emitted from the laser light source 23a are made incident; and a coupler 23c (coupling member) which couples the laser beams guided by the light guide members 23b. The second light source 23 further includes a light guide member 23d which guides a laser beam coupled by the coupler 23c. One light guide member 23b is optically connected to one LD. Each of the light guide members 23b and 23d includes, for example, a single optical fiber.

As illustrated in FIG. 1, FIG. 3A and FIG. 3B, the first light source module 20 further includes a first collimator 25 (first collimation member) including a lens which converts LED light emitted from the first light source 21 to a first parallel beam; and a second collimator 27 (second collimation member) including a lens which converts a laser beam emitted from the second light source 23 to a second parallel beam.

The laser beam is incident on the second collimation beam 27 in the state in which the laser beam has a divergence angle corresponding to a reception angle (NA) of the light guide member 23d. The second collimation beam 27 converts the laser beam in this state to a parallel beam.

The relative distance between the first light source 21 and first collimator 25 and the relative distance between the second light source 23 and second collimator 27 are adjusted as desired, such that the light beam diameter of the first parallel beam and the light beam diameter of the second parallel beam become identical to each other.

As illustrated in FIG. 1, FIG. 3A and FIG. 3B, the first light source module 20 further includes a coupler 29 (coupling member) which is disposed in front of the first collimator 25 and second collimator 27 in directions of travel of light, and couples the LED light, which is the first parallel beam, and the laser beam which is the second parallel beam. The coupler 29 couples such that an optical axis of the LED light and an optical axis of the laser beam agree with each other. Thus, the coupler 29 further includes a mirror 29a which is disposed at an intersection between the LED light and the laser beam, partially reflects, or reflects, the LED light toward a light source-side connection hole 37 (light source-side connection hole portion) (to be described later), and transmits through the laser beam toward the light source-side connection hole 37. The mirror 29a includes, for example, a dichroic mirror. The mirror 29a is disposed, for example, at an angle of 45° to the optical axis of the LED light and the optical axis of the laser beam. In the meantime, when the first light source 21 and second light source 23 are reversely disposed, use is made of, as the mirror 29a, a mirror which transmits through the LED light toward the light source-side connection hole 37, and totally reflects the laser beam toward the light source-side connection hole 37. According to the above, the LED light and laser beam can be coupled by the mirror 29a.

As described above, the light beam diameter of the first parallel beam and the light beam diameter of the second parallel beam are made identical to each other, by the relative distance between the first light source 21 and first collimator 25 and the relative distance between the second light source 23 and second collimator 27. Thus, the coupler 29 couples the LED light and laser beam such that the light beam diameter of the LED light, which is the first parallel beam, and the light beam diameter of the laser beam, which is the second parallel beam, become identical to each other. The coupler 29 couples the LED light and laser beam such that the entire light beam of the LED light, which is the first parallel beam, overlaps the entirety of the laser beam, which is the second parallel beam. The coupler 29 may couple the LED light and laser beam such that the light distribution angle of the LED light and the light distribution angle of the laser beam agree with each other.

As illustrated in FIG. 1, FIG. 3A and FIG. 3B, the first light source module 20 further includes a light focusing member 31 which focuses the light coupled by the coupler 29 toward the light source-side connection hole 37. Specifically, the light focusing member 31 focuses the light onto an irradiation-side optical connector 53, 73 (irradiation-side optical connection portion) of the irradiation module 50, 70, which is placed in a light source-side optical connector 37a (light source-side optical connection portion) of the light source-side connection hole 37. The light focusing member 31 is disposed in front of the coupler 29 in the direction of travel of light. The light focusing member 31 is shared by the first light source 21 and second light source 23. The light focusing member 31 includes, for example, a lens.

As illustrated in FIG. 1, FIG. 3A and FIG. 3B, the first light source module 20 further includes a determination unit 33 (determination circuit) which determines the irradiation module 50, 70 which is connected to the light source module. The determination unit 33 determines whether the irradiation module, which is connected to the first light source module 20, is the first irradiation module 50 or the second irradiation module 70, based on information stored in a storage unit 57, 77 (to be described later) which the irradiation module 50, 70 includes. The determination unit 33 has, for example, a hardware circuitry including ASIC.

As illustrated in FIG. 1, FIG. 3A and FIG. 3B, the first light source module 20 further includes a light source controller 35 which controls at least one of the first light source 21 and the second light source 23, based on a determination result of the determination unit 33. The light source controller 35 has, for example, a hardware circuitry including ASIC.

As illustrated in FIG. 1, FIG. 3A and FIG. 3B, the first light source module 20 further includes the light source-side connection hole 37 to/from which a coupling connector 15*a* that is disposed on a universal cord 15 of the endoscope 13 is attached/detached, and which functions as a receptacle portion of the light source device 11. The light source-side connection hole 37 is shared and made common to a first irradiation-side connector 51 (first irradiation-side connection portion) and second irradiation-side connector 71 (second irradiation-side connection portion), such that the light source-side connection hole 37 is detachably connectable to the first irradiation-side connector 51 mounted on the first irradiation module 50 and to the second irradiation-side connector 71 mounted on the second irradiation module 70. For example, the light source-side connection hole 37 is mechanically detachably attached to the first irradiation-side connector 51 and second irradiation-side connector 71 in the respective irradiation modules 50 and 70 which are various kinds of modules with mutually different optical functions, and the light source-side connection hole 37 is a common member to the first irradiation-side connector 51 and second irradiation-side connector 71. Hence, the light source-side connection hole 37, which is connected to the first irradiation-side connector 51, is the same part as the light source-side connection hole 37 which is connected to the second irradiation-side connector 71, and is disposed at the same position as the light source-side connection hole 37 which is connected to the second irradiation-side connector 71. Thus, the light source-side connection hole 37 positions the first irradiation-side connector 51 and second irradiation-side connector 71, such that the position of the optical axis of the first irradiation-side connector 51 at a time when the light source-side connection hole 37 is connected to the first irradiation-side connector 51 agrees with the position of the optical axis of the second irradiation-side connector 71 at a time when the light source-side connection hole 37 is connected to the second irradiation-side connector 71.

As illustrated in FIG. 1, FIG. 3A and FIG. 3B, the light source-side connection hole 37 includes a light source-side optical connector 37*a* which is connected to the irradiation-side optical connector 53, 73 of the irradiation-side connector 51, 71; and a light source-side electrical connector 37*b* (light source-side electrical connection portion) which is connected to an irradiation-side electrical connector 55, 75 (irradiation-side electrical connection portion) of the irradiation-side connector 51, 71. The connection between the light source-side optical connector 37*a* and the irradiation-side optical connector 53, 73 is made at the same time as the connection between the light source-side electrical connector 37*b* and the irradiation-side electrical connector 55, 75.

The light source-side optical connector 37*a* is disposed coaxial with, for example, the light focusing member 31, and is disposed coaxial with a position at which the light focused by the light focusing member 31 is focused. The light source-side optical connector 37*a* includes a through-hole through which the irradiation-side optical connector 53, 73 penetrates.

The light source-side electrical connector 37*b* is connected to the determination unit 33.

[Irradiation Module]

As described above, the irradiation modules include the first irradiation module 50 and second irradiation module 70 as illustrated in FIG. 1, FIG. 3A and FIG. 3B. A brief description will be given below of common parts between the first irradiation module 50 and second irradiation module 70.

The irradiation module 50, 70 includes the irradiation-side connector 51, 71 which is connected to the light source-side connection hole 37 and on which light emitted from the light source-side connection hole 37 is made incident at a time of connection; a light guide member 61, 81 which guides the light that is made incident from the irradiation-side connector 51, 71; and an emitter 63, 83 (emission unit) which emits to an outside the light guided by the light guide member 61, 81.

Hereinafter, concrete structures of the first irradiation module 50 and second irradiation module 70 of the irradiation modules will be described.

The first irradiation module 50 functions as a bundle fiber scope. In the first irradiation module 50, the first irradiation-side connector 51, the first light guide member 61 and the first emitter 63 are mounted.

The second irradiation module 70 functions as a single fiber scope. In the second irradiation module 70, the second irradiation-side connector 71, the second light guide member 81 and second emitter 83 are mounted.

Each of the first irradiation-side connector 51 and second irradiation-side connector 71 is disposed in the coupling connector 15*a* which is disposed, for example, on the universal cord 15 of the endoscope 13. Each of the first light guide member 61 and second light guide member 81 is disposed in the inside of the universal cord 15, an operation section 17 and a soft insertion section 19 of the endoscope 13. Each of the first emitter 63 and second emitter 83 is disposed a distal end portion of the insertion section 19.

The endoscope 13, in which the first irradiation module 50 is mounted, is a separate body from the endoscope 13 in which the second irradiation module 70 is mounted.

A greatest difference between the first irradiation module 50 (bundle fiber scope) and second irradiation module 70 (single fiber scope) is that their optical functions, for example, are different from each other, and, specifically, the kinds of their light guide members 61 and 81 are different from each other.

For example, the first light guide member 61 includes a bundle fiber 61*a* which is formed by bundling a plurality of optical fiber strands, and the second light guide member 18 includes a single optical fiber 81*a*, such that an effective cross-sectional area of the second light guide member 81 becomes smaller than a light-guide cross-sectional area of the first light guide member 61. The effective cross-sectional area indicates a cross section perpendicular to the center axis of the light guide member 61, 81, and indicates a light emission area.

In the bundle fiber 61*a*, the optical fiber strand includes a core portion (not shown) disposed at a central part of the single optical fiber, and a clad portion (not shown) disposed in a manner to cover the core portion. The diameter of the core portion is several μm to several-ten μm. The refractive index of the clad portion is lower than the refractive index of the core portion. Thus, light is reflected by an interface between the core portion and clad portion, confined in the core portion, and guided by the core portion. Thereby, the optical fiber strand confines the light in the inside of the optical fiber strand, and transmits the light to the first emitter 63 without leaking the light. The diameter of the bundle fiber 61*a* is, for example, about several mm.

The single optical fiber 81*a* includes a core portion (not shown) disposed at a central part of the single optical fiber 81*a*, and a clad portion (not shown) disposed in a manner to cover the core portion. The diameter of the core portion is several µm to several-hundred µm. The refractive index of the clad portion is lower than the refractive index of the core portion. Thus, light is reflected by an interface between the core portion and clad portion, confined in the core portion, and guided by the core portion. Thereby, the optical fiber 81a confines the light in the inside of the optical fiber 81a, and transmits the light to the second emitter 83 without leaking the light.

[Detailed Structure of First Radiation Module 50 (Bundle Fiber Scope)]

As illustrated in FIG. 1 and FIG. 3A, the first irradiation-side connector 51 includes a first irradiation-side optical connector 53 which is connected to the light source-side optical connector 37a; a first irradiation-side electrical connector 55 which is connected to the light source-side electrical connector 37b; and a first storage unit 57 (first storage).

As illustrated in FIG. 1 and FIG. 3A, the first irradiation-side optical connector 53 includes a cover glass 53a on which the light focused by the light focusing member 31 is made incident, when the first irradiation-side optical connector 53 is connected to the light source-side optical connector 37a; and a rod lens 53b which is disposed in rear of the cover glass 53a in the direction of travel of light, and is optically connected to one end portion of the bundle fiber 61a.

The cover glass 53a is formed of a light-transmissive material.

The rod lens 53b includes a core portion (not shown) disposed at a central part of the rod lens 53b, and a clad portion (not shown) disposed in a manner to cover the core portion. The refractive index of the clad portion is lower than the refractive index of the core portion. Thus, light is reflected by an interface between the core portion and clad portion, confined in the core portion, and guided by the core portion. Thereby, the rod lens 53b confines the light in the inside of the rod lens 53b, and transmits the light to the bundle fiber 61a without leaking the light. The diameter of the rod lens 53b is substantially equal to the diameter of the bundle fiber 61a. The rod lens 53b uniformizes the light intensity in the cross section in a direction perpendicular to the optical axis of light. This light indicates the light that is made incident on the first irradiation-side optical connector 53 from the first light source module 20.

In general, the light intensity of a laser beam is strong at a central part of the laser beam, and becomes weaker away from the central part. In this manner, the light intensity of the laser beam is nonuniform. If the laser beam is directly made incident on the bundle fiber 61a in this state, a variance occurs among the amounts of light incident on the respective optical fibers of the bundle fiber 61a. In addition, a deviation occurs in the light intensity of the laser beam emitted from the bundle fiber 61a, and nonuniformity in luminance or nonuniformity in light distribution occurs in illumination light. However, by the rod lens 53b, the laser beam is repeatedly reflected within the rod lens 53b, and the laser beam is incident, with no variance, on the bundle fiber 61a. Thus, the deviation in light intensity of the laser beam is eliminated, and the light intensity becomes uniform. Therefore, nonuniformity in luminance or nonuniformity in light distribution is prevented.

The first storage unit 57 as illustrated in FIG. 1 and FIG. 3A stores information to the effect that the irradiation module is the first irradiation module 50. When the first irradiation-side electrical connector 55 is connected to the light source-side electrical connector 37b, the first storage unit 57 transmits the information to the determination unit 33 via the first irradiation-side electrical connector 55 and light source-side electrical connector 37b.

As illustrated in FIG. 1 and FIG. 3A, the first emitter 63 includes an optical conversion member 63a which is disposed at the other end portion of the first irradiation module 50 and is optically connected to the other end portion of the bundle fiber 61a. The optical conversion member 63a includes a lens system which converts the light, which is emitted from the other end portion of the bundle fiber 61a, to illumination light having a desired light distribution and divergence angle, and irradiates the illumination light. In general, since the divergence angle of the light emitted from the end portion of the bundle fiber 61a is small, the optical conversion member 63a increases this divergence angle.

[Detailed Structure of Second Radiation Module 70 (Single Fiber Scope)]

As illustrated in FIG. 1 and FIG. 3B, the second irradiation-side connector 71 includes a second irradiation-side optical connector 73 which is connected to the light source-side optical connector 37a; a second irradiation-side electrical connector 75 which is connected to the light source-side electrical connector 37b; and a second storage unit 77 (second storage). The position of the second irradiation-side connector 71 in the second irradiation module 70 is identical to the position of the first irradiation-side connector 51 in the first irradiation module 50.

As illustrated in FIG. 1 and FIG. 3B, the second irradiation-side optical connector 73 includes a cover glass 73a on which the light converged by the light focusing member 31 is made incident, when the second irradiation-side optical connector 73 is connected to the light source-side optical connector 37a; and a light focusing member 73b which is disposed in rear of the cover glass 73a and is optically connected to one end portion of the single optical fiber 81a.

The cover glass 73a is formed of a light-transmissive material.

The light focusing member 73b focuses light on the single optical fiber 81a such that the light, which has transmitted through the cover glass 73a, may be made incident on the single optical fiber 81a. In the optical fiber 81a, since the diameter of the core portion is several µm to several-hundred µm, a positional displacement leads to great optical loss. The optical loss is prevented by the light focusing member 73b being disposed also on the irradiation module side.

The second storage unit 77 as illustrated in FIG. 1 and FIG. 3B stores information to the effect that the irradiation module is the second irradiation module 70. When the second irradiation-side electrical connector 75 is connected to the light source-side electrical connector 37b, the second storage unit 77 transmits the information to the light source controller 35 via the second irradiation-side electrical connector 75 and light source-side electrical connector 37b.

Figure 2:
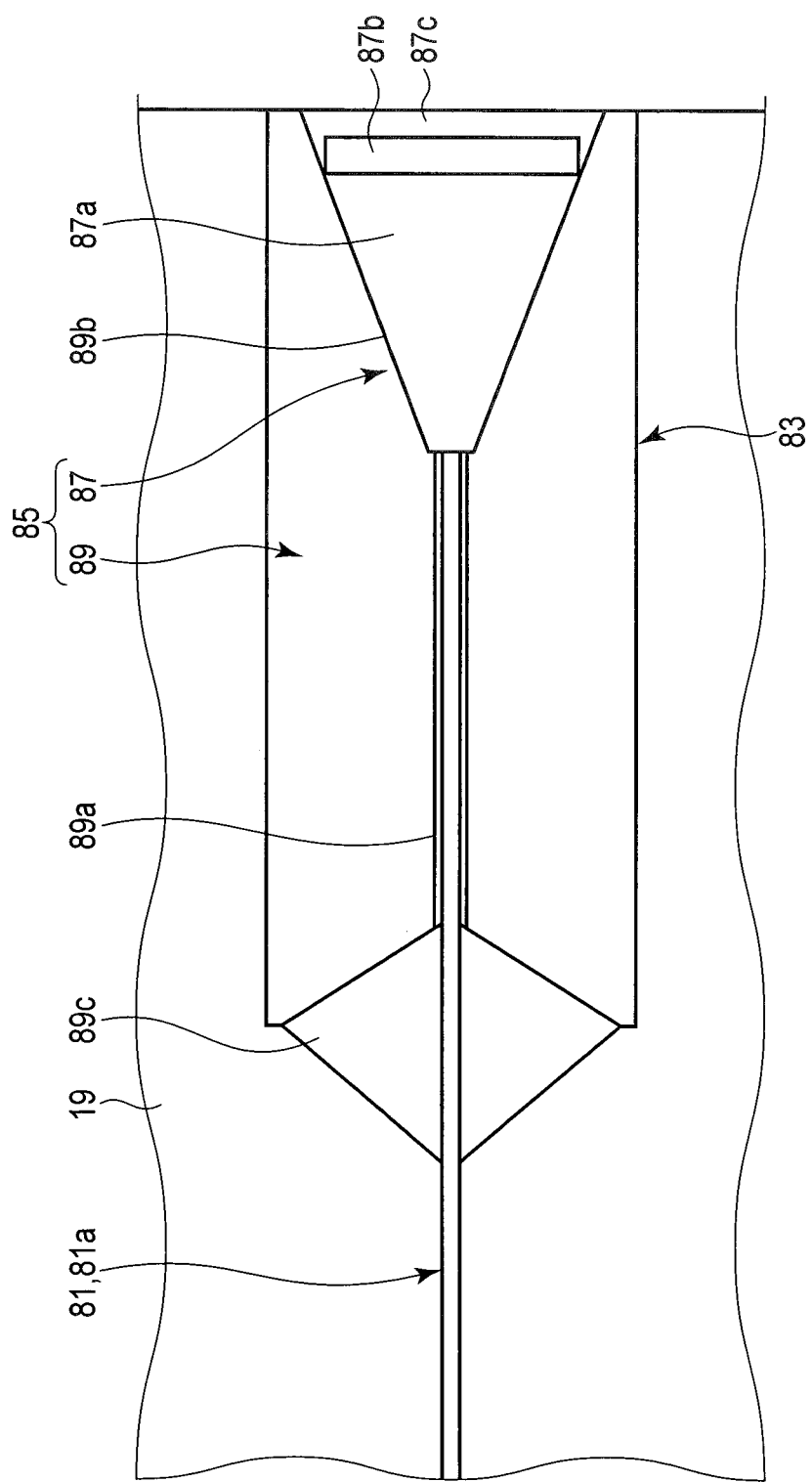
FIG. 2 is a view illustrating the structure of a second emitter.

As illustrated in FIG. 2, the second emitter 83 includes an optical conversion unit 85 which is disposed at the other end portion of the second irradiation module 70 and is optically connected to the other end portion of the single optical fiber 81a.

The optical conversion unit 85 as illustrated in FIG. 2 includes a wavelength converter 87 which converts, as desired, the wavelength of light which is emitted from the other end portion of the single optical fiber 81a; and a holding member 89 including a first holding hole 89a (first holding hole portion) which holds the other end portion of the single optical fiber 81a, and a second holding hole 89b (first holding hole portion) which holds the wavelength converter 87.

The wavelength converter 87 includes a transparent member 87a having, for example, a truncated conical shape; a fluorescent body 87b which is disposed within the transparent member 87a, converts the wavelength of light, and emits fluorescence; and a diffusion member 87c which diffuses the fluorescence emitted from the fluorescent body 87b. The transparent member 87a is formed of a member with high transmissivity to a laser beam. The fluorescent body 87b is formed of a ceramic of, e.g. YAG:Ce. The fluorescent body 87b is excited by an irradiated laser beam, and emits lights with different wavelengths. The fluorescent body 87b emits light in all directions. Thus, part of the light travels back to the optical fiber 81a side, but the light, which travels back, is reflected by the taper-shaped second holding hole 89b toward the distal end portion side of the second irradiation module 70. Part of the laser beam, which is irradiated on the fluorescent body 87b, transmits through the fluorescent body 87b. The fluorescence emitted from the fluorescent body 87b and the laser beam transmitting through the fluorescent body 87b are diffused by the diffusion member 87c, illuminate a target object, and are utilized as white illumination.

Here, the optical conversion unit 85 is not limited to the above structure. The optical conversion unit 85 has characteristics with a function of converting the peak wavelength, spectrum shape, light distribution angle, light amount, etc., with respect to the optical properties of the light that is incident on the optical conversion unit 85 from the single optical fiber 81a.

The holding member 89 holds, within the holding member 89, the other end portion of the single optical fiber 81a and the wavelength converter 87 by the first holding hole 89a and second holding hole 89b, such that the other end portion of the single optical fiber 81a and the wavelength converter 87 are optically coupled in the inside of the holding member 89. The holding member 89 functions as, for example, a sleeve. The other end portion of the single optical fiber 81a is adhered to an end face portion of the holding member 89 by an adhesive 89c. The first holding hole 89a has a cylindrical shape, and the second holding hole 89b has a taper shape.

[Operation]

Hereinafter, a description is given of the connection between the first light source module 20 and the first irradiation module 50 (bundle fiber scope), and the connection between the first light source module 20 and the second irradiation module 70 (single fiber scope).

By the above-described connection, the endoscope light source system 10 includes light guide routes which include the light source, the light source-side connection hole 37, the irradiation-side connector, the light guide member and the emitter, and which are optical paths for passage of light.

For the purpose of convenience, the following is defined in the connection between the first light source module 20 and the first irradiation module 50 illustrated in FIG. 3A.

A light guide route, which includes the first light source 21, the light source-side connection hole 37, the first irradiation-side connector 51, the first light guide member 61 and the first emitter 63, is defined as a first light guide route 201.

A light guide route, which includes the second light source 23, the light source-side connection hole 37, the first irradiation-side connector 51, the first light guide member 61 and the first emitter 63, is defined as a third light guide route 203.

A light guide route, which includes the first light source 21, the second light source 23, the light source-side connection hole 37, the first irradiation-side connector 51, the first light guide member 61 and the first emitter 63, is defined as a fourth light guide route 204.

For the purpose of convenience, the following is defined in the connection between the first light source module 20 and the second irradiation module 70 illustrated in FIG. 3B.

A light guide route, which includes the second light source 23, the light source-side connection hole 37, the second irradiation-side connector 71, the second light guide member 81 and the second emitter 83, is defined as a second light guide route 202.

In addition, the light source-side connection hole 37 is shared and made common to the first irradiation-side connector 51 and second irradiation-side connector 71, such that the first light guide route 201, the second light guide route 202, the third light guide route 203 and the fourth light guide route 204 can be constituted.

[Connection Between First Light Source Module 20 and First Irradiation Module 50 (Bundle Fiber Scope)]

As illustrated in FIG. 3A, if the first irradiation-side connector 51 is inserted in the light source-side connection hole 37, the light source-side optical connector 37a is connected to the first irradiation-side optical connector 53, and the light source-side electrical connector 37b is connected to the first irradiation-side electrical connector 55. These connections are implemented at the same time. At the same time, the first storage unit 57 transmits the information to the determination unit 33 via the first irradiation-side electrical connector 55 and light source-side electrical connector 37b. This information includes information to the effect that the irradiation module is the first irradiation module 50. Based on this information, the determination unit 33 determines that the irradiation module, which is connected to the first light source module 20, is the first irradiation module 50, and transmits the determination result to the light source controller 35. Based on this determination result, the light source controller 35 controls the LED light source 21a and laser light source 23a.

In normal optical observation, the first light guide route 201 is used. Specifically, by the control of the light source controller 35, the LED light source 21a is driven, and white LED light is emitted. The white LED light irradiates a target object via the first collimator 25, coupler 29, light focusing member 31, cover glass 53a, rod lens 53b, first light guide member 61 (bundle fiber 61a) and optical conversion member 63a. The white LED light is white light.

In special optical observation, the third light guide route 203 is used. Specifically, by the control of the light source controller 35, the LD in the laser light source 23a, which emits a laser beam with a wavelength of 405 nm, and the LD, which emits a laser beam with a wavelength of 515 nm, are driven, and a laser beam with a wavelength of 405 nm and a laser beam with a wavelength of 515 nm are emitted. The laser beam irradiates a target object via the light guide member 23b, coupler 23c, light guide member 23d, second collimator 27, coupler 29, light focusing member 31, cover glass 53a, rod lens 53b, first light guide member 61 (bundle fiber 61a) and optical conversion member 63a. The laser beam is special light.

The target object, which is illuminated by the white light or special light, is imaged by an imaging unit (not shown) which is disposed at a distal end portion of the insertion section 19, and is displayed as an observation image on a display unit (not shown) which is connected to the coupling connector 15a.

In the meantime, in the above, for example, if the LED light source 21a and laser light source 23a are driven individually and independently, the normal optical observation and special optical observation are individually implemented. In addition, a normal optical image, which is an observation image in the normal optical observation, is displayed on the display unit, and a special optical image, which is an observation image in the special optical observation, is displayed on the display unit.

For example, if the LED light source 21a and laser light source 23a are simultaneously driven, the white light and special light are simultaneously made incident on the first irradiation module 50 in the fourth light guide route. In this manner, the white light and special light may be mixed and used. Thereby, the display unit can display, in a superimposed manner, the special optical image, which was obtained by the special light and in which blood vessels are emphasized, upon the normal optical image obtained by the white light.

If the light source controller 35 switches at high speed the driving of the LED light source 21a and the driving of the laser light source 23a, that is, if the first light guide route 201 and third light guide route 203 are switched at high speed, the white light and special light are alternately emitted, and the white light and special light are made incident on the first irradiation module 50 alternately at high speed. Thereby, the normal optical image obtained by the white light and the special optical image obtained by the special light can be acquired during one frame captured by the imaging unit. In addition, the display unit can display these two observation images on one screen. The above applies similarly to the fourth light guide route.

The above is controlled, for example, by the light source controller 35. In this manner, the LED light and laser beam are selectively used in accordance with various purposes of use for observation.

In this manner, in this connection state, one of the following is selected:

the first light guide route 201 along which, with only the LED light source 21a being driven, the LED light is guided from the LED light source 21a to the optical conversion member 63a via the bundle fiber 61a, etc.;

the third light guide route 203 along which, with only the laser light source 23a being driven, the laser beam is guided from the laser light source 23a to the optical conversion member 63a via the bundle fiber 61a, etc.; and the fourth light guide route 204 along which, with the LED light source 21a and laser light source 23a being driven, the LED light and the laser beam are guided from the LED light source 21a and laser light source 23a to the optical conversion member 63a via the bundle fiber 61a, etc.

[Connection Between First Light Source Module 20 and Second Radiation Module 70 (Single Fiber Scope)]

As illustrated in FIG. 3B, if the second irradiation-side connector 71 is inserted in the light source-side connection hole 37, the light source-side optical connector 37a is connected to the second irradiation-side optical connector 73, and the light source-side electrical connector 37b is connected to the second irradiation-side electrical connector 75. These connections are implemented at the same time. At the same time, the second storage unit 77 transmits the information to the determination unit 33 via the second irradiation-side electrical connector 75 and light source-side electrical connector 37b. This information includes information to the effect that the irradiation module is the second irradiation module 70. Based on this information, the determination unit 33 determines that the irradiation module, which is connected to the first light source module 20, is the second irradiation module 70, and transmits the determination result to the light source controller 35. Based on this determination result, the light source controller 35 controls the laser light source 23a.

In this case, the second light guide route 202 is used. Specifically, by the control of the light source controller 35, the LD in the laser light source 23a, which emits a laser beam with a wavelength of 405 nm, and the LD, which emits a laser beam with a wavelength of 445 nm, are driven, and a laser beam with a wavelength of 405 nm and a laser beam with a wavelength of 445 nm are emitted. The laser beam irradiates a target object via the light guide member 23b, coupler 23c, light guide member 23d, second collimator 27, coupler 29, light focusing member 31, cover glass 73a, light focusing member 73b, single optical fiber 81a and optical conversion unit 85. In the meantime, the laser beams are coupled in the coupler 23c and converted to white light.

Incidentally, in this connection state, it is possible that only the LED light source 21 is driven and LED light is guided to the optical conversion unit 85 by the single optical fiber 81a. However, when light with a large light emission point, such as LED light, is incident on a small light guide such as the single optical fiber 81a, light loss increases, and there is concern that a sufficient amount of light does not reach the optical conversion member 63a. Thus, the merit of using this structure is small.

Thus, in this connection state, only the laser light source 23a is driven, and the second light guide route 202 is formed, along which the laser beam is guided from the second light source 23 to the optical conversion unit 85 via the single optical fiber 81a, etc.

Advantageous Effects

As described above, in the present embodiment, the first light source module 20, which includes the first light source 21 and second light source 23, is shared and made common to the first irradiation module 50 and second irradiation module 70. In addition, the light source-side connection hole 37 of the first light source module 20 is a common member, which is shared between the first irradiation-side connector 51 of the first irradiation module 50, which is connected to the light source-side connection hole 37, and the second irradiation-side connector 71 of the second irradiation module 70, which is connected to the light source-side connection hole 37. Therefore, in the present embodiment, it is possible to provide the first light source module 20 which can reduce time and labor for the connection to various kinds of irradiation modules 50, 70, and the endoscope light source system 10 including this first light source module 20. Furthermore, in this embodiment, since the light source-side connection hole 37 of the first light source module 20 is common to irradiation modules 50 and 70 and is disposed at the same position, the time and labor for the connection can be reduced.

In the present embodiment, the light source-side connection hole 37 is made common to the first irradiation-side connector 51 and second irradiation-side connector 71, such that the first light guide route 201, second light guide route 202, third light guide route 203 and fourth light guide route 204 can be constituted. Thus, in this embodiment, even if the first irradiation module 50 and second irradiation module 70 have mutually different optical functions, the first irradiation module 50 and second irradiation module 70 can exhibit performances.

In the meantime, in general, for the light sources having mutually different optical characteristics, such as the first light source 21 and second light source 23, if use is made of the light source-side connection holes 37, irradiation-side connectors 51, 71 and light guide members 61, 81, which are made to match with the respect optical characteristics, the flexibility in application uses deteriorates.

Specifically, the characteristics of the first light source 21 which emits scattered light, such as LED light or lamp light, are different from the characteristics of the second light source 23 which emits coherent light such as a laser beam.

To begin with, as regards the light emission area, the lamp light is largest, the LED light is second largest, and laser beam is smallest. If the light emission area is large, even if an optical element such as a lens is used, the light beam diameter cannot be reduced to focus on an area smaller than the effective light emission area.

In other words, it is difficult for LED light or lamp light with a large light emission area to be efficiently made incident on the single optical fiber 81a with a small cross-sectional area. Necessarily, the bundle fiber 61a with a large cross-sectional area is used for the LED light or lamp light with a large light emission area.

By contrast, a laser beam with a very small light emission area can be incident on the single optical fiber with a small cross-sectional area with high efficiency. Thus, the single optical fiber with a small cross-sectional area is used for the laser beam with a very small light emission area.

As regards the divergence angle of light, the lamp light is widest, the LED light is second widest, and laser beam is narrowest. Thus, the bundle fiber 61a with a large reception angle (NA) is used for the lamp light or LED light. The single optical fiber 81a with a small reception angle (NA) is used for the laser beam.

As described above, the light guide members 61 and 81, which are used, are different from each other, in accordance with the light sources 21 and 23. As a result, in general, in the first light source module 20, for example, the light source-side connection hole 37, which is connected to the first irradiation module 50, is disposed as a separate body from the light source-side connection hole 37, which is connected to the second irradiation module 70. Thus, the first light source module becomes heavier, and the scope needs to be connected by visually distinguishing the light source-side connection hole 37. As a result, a load is imposed on the user.

However, in the present embodiment, as described above, the light source-side connection hole 37 of the first light source module 20 is common to the irradiation modules 50 and 70, and is disposed at the same position. Thus, deterioration in flexibility in application uses can be prevented, and the first light source module 20 can have compatibility. There is no need to provide the same number of light source-side connection holes 37 as the number of irradiation modules 50, 70, the load on the user can be alleviated, the first light source module 20 can be reduced in size, and the cost of the first light source module 20 can be reduced.

As regards the spectrum shape, the lamp light has a largest spectrum width, the LED light has a second largest spectrum width, and the laser beam has a smallest spectrum width. By these lights being combined, the degree of freedom of the spectrum shape of illumination light, which is usable for diagnosis, etc., can be remarkably enhanced.

Specifically, in normal optical observation, lamp light or LED light having a broad spectrum shape is suitable. However, in special optical observation using only a specific wavelength, a laser beam having a narrow spectrum shape is needed. Thus, as described above, the present embodiment is very effective, in which lamp light or LED light, and a laser beam are simultaneously used, or lamp light or LED light, and a laser beam are quickly switched and used.

From this viewpoint, by various kinds of light sources 21, 23 being mounted in the first light source module 20, the first light source module 20 can adapt to various purposes of use for observation. By preparing one first light source module 20, the user can selectively use the irradiation module 50, 70 in accordance with the purpose of use, and can perform various diagnoses, etc.

In the present embodiment, the first light guide member 61 includes the bundle fiber 61a and the second light guide member 81 includes the single optical fiber 81a, such that the effective cross-sectional area of the second light guide member 81 becomes smaller than the light-guide cross-sectional area of the first light guide member 61. Thus, the first irradiation module 50 functions as a bundle fiber scope, and the second irradiation module 70 functions as a single fiber scope.

Thereby, in the present embodiment, the first, third and fourth light guide routes are formed by the first irradiation module 50, and the second light guide route 202 is formed by the second irradiation module 70, thus being able to adapt to various purposes of use for observation.

When the second irradiation module 70 is used, the laser beam is made incident on the single optical fiber 81a by the light focusing member 31 with high efficiency. Thus, in the second irradiation module 70, a high optical coupling efficiency can be obtained with reduced power consumption, and with no optical loss. By the single optical fiber 81a with the thickness of several-hundred μm, substantially the same amount of light as with the bundle fiber 61a with the thickness of several mm can be transmitted to the optical conversion unit 85, and the insertion section 19 can be reduced in thickness. In the case where the insertion section 91 is thin, the second irradiation module 70 is used, and thereby a large amount of illumination light can be obtained.

In the present embodiment, the light source-side connection hole 37 positions the first irradiation-side connector 51 and second irradiation-side connector 71, such that the position of the optical axis of the first irradiation-side connector 51 agrees with the position of the optical axis of the second irradiation-side connector 71. Thus, in this embodiment, most parts of the structure of the first irradiation module 50 and the structure of the second irradiation module 70 can be made uniform.

In the present embodiment, if the white light and special light are simultaneously made incident on the first irradiation module 50, a special optical image can be superimposed on a normal optical image.

In this embodiment, if the white light and special light are alternately made incident on the first irradiation module 50 at high speed, a normal optical image and a special optical image can be displayed on one screen.

In this manner, the present embodiment can adapt to various purposes of use for observation.

In the present embodiment, by the coupler 29, various kinds of first light source 21 and second light source 23 can be used, thus being able to adapt to various purposes of use for observation.

In the present embodiment, by the coupler 29, the optical axis of the LED light agrees with the optical axis of the laser beam. Thereby, when the LED light and laser beam are incident on the first irradiation module 50, the uniformity in incidence efficiency and light intensity can be improved.

In the present embodiment, by the mirror 29a, the degree of freedom of the position of disposition of the first light source 21 and second light source 23 can be enhanced.

In this embodiment, by the coupler 29, the light beam diameter of the LED light and the light beam diameter of the laser beam become identical to each other. Thereby, when the LED light and laser beam are incident on the first irradiation module 50, the uniformity in incidence efficiency and light intensity can be improved.

In the present embodiment, the relative distance between the first light source 21 and first collimator 25 and the relative distance between the second light source 23 and second collimator 27 are adjusted as desired. Thereby, in this embodiment, the light beam diameter of the first parallel beam and the light beam diameter of the second parallel beam can be made identical to each other. Thereby, when the LED light and laser beam are incident on the first irradiation module 50, the uniformity in incidence efficiency and light intensity can be improved.

In the present embodiment, by the coupler 29, the light distribution angle of the LED light and the light distribution angle of the laser beam agree with each other. Thereby, when the LED light and laser beam are incident on the first irradiation module 50, the uniformity in incidence efficiency and light intensity can be improved.

By the above, in the normal optical observation and special optical observation, the occurrence of displacement can be prevented.

For example, in the first irradiation module 50, if the bundle fiber 61a for a laser beam is a separate body from the bundle fiber 61a for LED light, and if the first emitter 63 for a laser beam is a separately body from the first emitter 63 for LED light, the insertion section 19 would become thicker, the number of members would increase, and the cost would increase. Since the first emitters 63 are different from each other, their light emission points are different from each other. As a result, in a normal optical observation image and a special optical observation image, deviation would occur in formation of shades or in color. However, in the present embodiment, even if the position of the first light source 21 and the position of the second light source 23 are different from each other, since the first light guide member 61 and first emitter 63 are made common in the first irradiation module 50, the above can be solved.

In the present embodiment, by the light focusing member 31, the LED light or laser beam can be made incident on the first irradiation module 50 or second irradiation module 70 with no waste.

In this embodiment, by the determination unit 33, the irradiation module, which is connected, can easily be determined.

In the present embodiment, by the light source controller 35, light corresponding to a purpose of use for observation can quickly be emitted by connecting the irradiation module to the light source module, for example, at the same time as the irradiation module is connected to the light source module.

[Others]

Figure 4A:
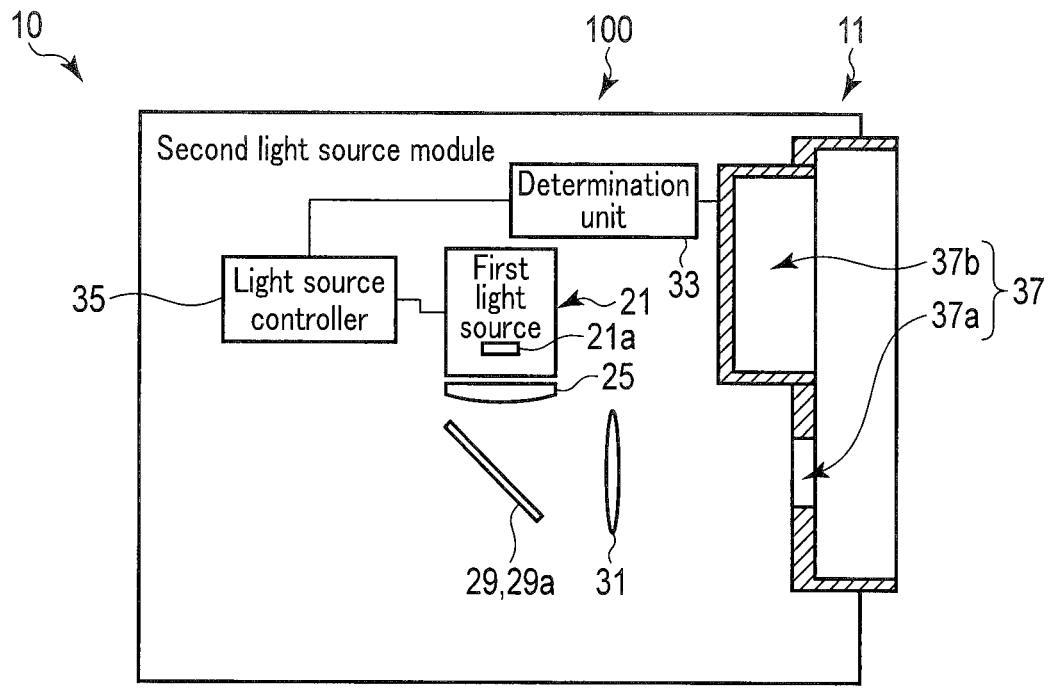
FIG. 4A is a view illustrating the structure of a second light source module.
Figure 4B:
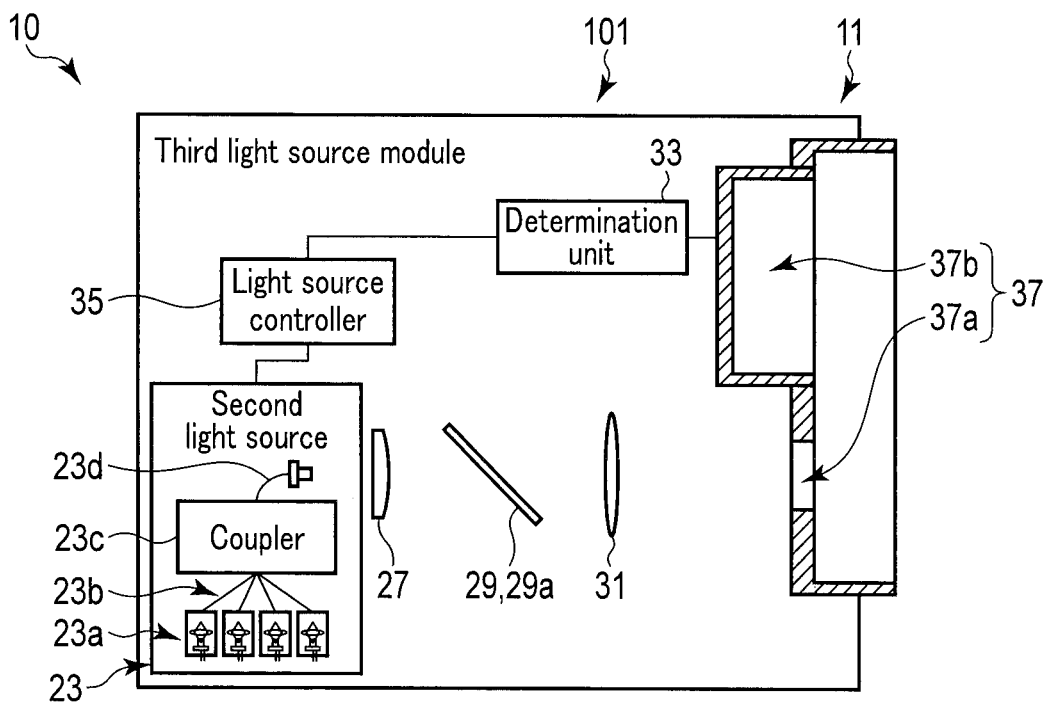
FIG. 4B is a view illustrating the structure of a third light source module.

It should suffice if the light source module includes any one of the first light source module 20 as illustrated in FIG. 1, a second light source module 100 in which only the first light source 21 is mounted as illustrated in FIG. 4A, and a third light source module 101 in which only the second light source 23 is mounted as illustrated in FIG. 4B.

It should suffice if the LED light source 21a emits white light. The white LED may be replaced with a plurality of LEDs which emit lights of mutually different wavelengths, and these lights may be coupled to produce white light.

The laser light source 23a may include a plurality of optimal LDs in accordance with purposes of use. The purposes of use indicate, for example, fluorescent observation or therapy such as PDT or PDD, oximetry, and pseudo-white observation by an RGB laser. The LDs emit lights with mutually different wavelengths or outputs. In particular, by plural LDs of different types being mounted, the light source module can adapt to various purposes of use.

The coupler 29 may include, in place of the mirror 29a, a half mirror or an optical system, for instance.

Second Embodiment

Figure 6A:
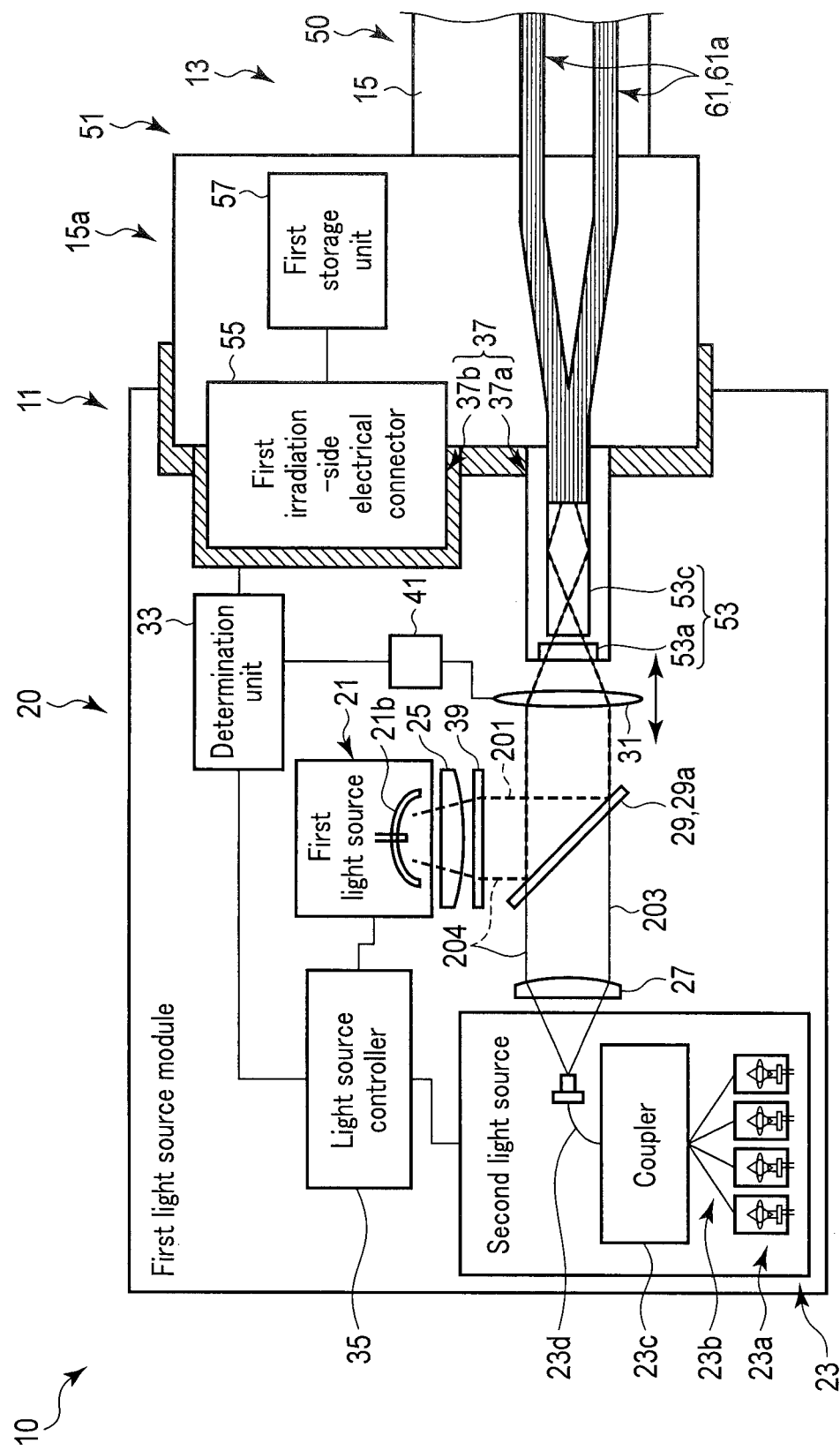
FIG. 6A is a view illustrating a state in which the first light source module shown in FIG. 5 is connected to a first irradiation module.
Figure 6B:
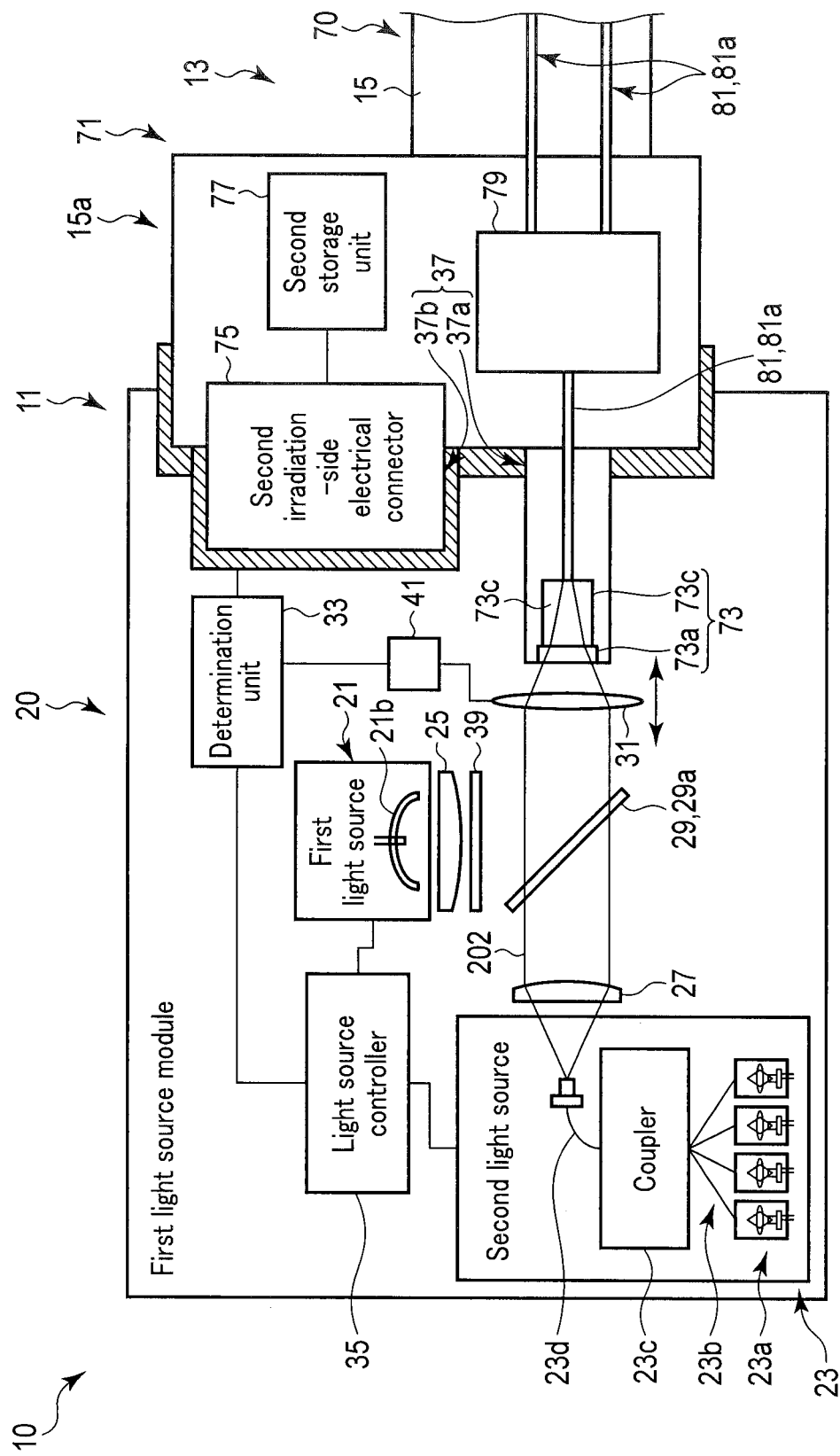
FIG. 6B is a view illustrating a state in which the first light source module shown in FIG. 5 is connected to a second irradiation module.

Referring to FIG. 5, FIG. 6A and FIG. 6B, only different points from the first embodiment will be described.

[First Light Source Module 20]

As illustrated in FIG. 5, in the first light source module 20, the first light source 21 includes, in place of the LED light source 21a, a lamp light source 21b such as a Xe lamp or a halogen lamp. The lamp light source 21b emits lamp light having very broad spectrum characteristics in a visible light region. Thus, in the present embodiment, in normal optical observation, a clear observation image can be obtained by lamp light than in the case where LED light of the LED light source 21a is used.

The first collimator 25 converts the lamp light, which is emitted from the lamp light source 21b, to parallel light.

The first light source module 20 includes a filter member 39 which is disposed between the first collimator 25 and mirror 29a and cuts off unnecessary light of the lamp light. The filter member 39 includes, for example, a cold filter which cuts off light of an infrared region, which is unnecessary light, or an RGB band-pass filter corresponding to an RGB field-sequential imaging method. Thereby, it is possible to adapt to not only photography by white light, but also to a scope of the RGB field-sequential imaging method.

The first light source module 20 includes an adjusting member 41 which adjusts, based on the determination result of the determination unit 33, at least one of the light distribution angle, intensity distribution and light beam diameter of the light which is incident on the irradiation-side connector 51, 71 from the light source 21, 23 in accordance with a light guide route. For the purpose of adjustment, the adjusting member 41 moves, for example, the light focusing member 31 in the direction of travel of light, and adjusts the position of the light focusing member 31. In the meantime, the adjusting member 41 may move the first collimator 25 or second collimator 27, and may adjust the position of the first collimator 25 or the position of the second collimator 27. The adjusting member 41 may include a movable lens system which is movable based on the determination result, such that the optimal light distribution angle, light intensity distribution or light beam diameter is realized in accordance with the scope.

By the above, for example, the light focusing member 31 can exactly focus light on the irradiation-side optical connector 53, 73 in accordance with the irradiation module 50, 70. In other words, by the movement of the light focusing member 31, the position of focus can be adjusted in accordance with the irradiation module 50, 70. Thereby, light can exactly be made incident on the light guide member 61, 81 with no waste.

In the meantime, the light focus is implemented by the length of the irradiation-side optical connector 53, 73 being adjusted as desired.

[First Radiation Module 50 and Second Radiation Module 70]

The first irradiation-side optical connector 53 includes a GRIN lens 53c in place of the rod lens 53b. The refractive index of a central part of the GRIN lens 53c is higher than the refractive index of a peripheral part around the central part.

The second irradiation-side optical connector 73 includes a GRIN lens 73c in place of the light focusing member 73b. The refractive index of a central part of the GRIN lens 73c is higher than the refractive index of a peripheral part around the central part.

The light guide member 61, 81 is branched into a plurality of parts.

In the first irradiation module 50, an end portion of the bundle fiber 61a is branched into two parts. In this case, the optical fiber is divided with a desired ratio.

In the second irradiation module 70, an optical coupler 79, which is a branching member which branches light, is disposed, for example, in the second irradiation-side connector 71. A plurality of single optical fibers 81a are connected to the optical coupler 79.

By the above, light is emitted from a plurality of locations at the end portion of the irradiation module 50, 70. Thereby, the distribution of illumination light on a subject can be uniformized, and nonuniformity in brightness in an observation image can be reduced.

The present invention is not limited directly to the above-described embodiments. At the stage of practicing the invention, the structural elements may be modified and embodied without departing from the spirit of the invention. Further, various inventions may be made by suitably combining a plurality of structural elements disclosed in the embodiments.

What is claimed is:

1. A light source module comprising:
   a light source-side connection hole configured to mechanically detachably attach to an irradiation-side connector of each of at least a first irradiation module and a second irradiation module, to combine the light source module with each of the at least first and second irradiation modules such that each combination emits illumination light corresponding to a different purpose of use,
   wherein:
   the first irradiation module comprises a first irradiation-side connector configured to be mechanically and detachably connected to the light source-side connection hole and on which light from the light source-side connection hole when connected is made incident, a first light guide member configured to guide the light from the first irradiation-side connector, and a first emitter configured to emit the light guided by the first light guide member;
   the second irradiation module comprises a second irradiation-side connector configured to be mechanically and detachably connected to the light source-side connection hole and on which light from the light source-side connection hole when connected is made incident, a second light guide member having an optical characteristic different from the first light guide member and configured to guide the light from the second irradiation-side connector, and a second emitter configured to emit the light guided by the second light guide member;
   the light source module comprises a first light source configured to produce a first light and a second light source configured to produce a second light, the first light source being a laser light source, the second light source being one of a LED light source and a lamp light source;
   the light source-side connection hole being common to the first irradiation-side connector and the second irradiation-side connector such that the light source-side connection hole is optically connectable to the first irradiation-side connector and the second irradiation-side connector to form a first light guide route, a second light guide route, a third light guide route, and a fourth light guide route, wherein
   the first light guide route being a first optical path including the first light source, the light source-side connection hole, the first irradiation-side connector, the first light guide member, and the first emitter,
   the second light guide route being a second optical path including the second light source, the light source-side connection hole, the second irradiation-side connector, the second light guide member, and the second emitter,
   the third light guide route being a third optical path including the second light source, the light source-side connection hole, the first irradiation-side connector, the first light guide member, and the first emitter,
   the fourth light guide route being a fourth optical path including the first light source and the second light source, the light source-side connection hole, the first irradiation-side connector, the first light guide member, and the first emitter,
   the first light guide route allows the first light from the first light source to enter the first irradiation module,
   the second light guide route allows the second light from the second light source to enter the second irradiation module,
   the third light guide route allows the second light from the second light source to enter the first irradiation module,
   the fourth light guide route allows the first light from the first light source and the second light from the second light source to one of simultaneously or alternately enter the first irradiation module;
   the illumination light for a normal optical image is emitted using only the first light from the first light source through the first light guide route; and
   the illumination light for a special optical image is emitted using only the second light from the second light source through the third light guide route.

2. The light source module according to claim 1, wherein the light source-side connection hole is configured to position the first irradiation-side connector and the second irradiation-side connector, such that a position of an optical axis of the first irradiation-side connector at a time when the light source-side connection hole is connected to the first irradiation-side connector agrees with a position of an optical axis of the second irradiation-side connector at a time when the light source-side connection hole is connected to the second irradiation-side connector.

3. The light source module according to claim 1, wherein the light source-side connection hole is disposed at a same position to the first irradiation module and the second irradiation module.

4. The light source module according to claim 2, wherein the second light source has a light emission area which is smaller than a light emission area of the first light source.

5. The light source module according to claim 4, wherein the light source module further includes an adjusting member configured to adjust, in accordance with the light guide route, at least one of a light distribution angle, an intensity distribution and a light beam diameter of the light which is incident on the irradiation-side connector from the light source module.

6. The light source module according to claim 1, wherein the first irradiation module includes an imaging sensor, and in the fourth light guide route, the first light emitted from the first light source and the second light emitted from the second light source are allowed to enter the first irradiation module alternately during one frame captured by the imaging sensor.

7. The light source module according to claim 1, further comprising a coupler configured to couple the first light and the second light.

8. The light source module according to claim 7, wherein the coupler is configured to couple such that an optical axis of the first light and an optical axis of the second light agree with each other.

9. The light source module according to claim 8, wherein the first light source and the second light source are disposed such that the optical axis of the first light and the optical axis of the second light cross perpendicular to each other, and the coupler includes a mirror disposed at a crossing part, and configured to reflect the first light and transmit through the second light, or configured to reflect the second light and transmit through the first light.

10. The light source module according to claim 7, wherein the coupler is configured to couple the first light and the second light such that a light beam diameter of the first light and a light beam diameter of the second light become identical to each other.

11. The light source module according to claim 10, further including a first collimator configured to convert the first light emitted from the first light source to first parallel light, and a second collimator configured to convert the second light emitted from the second light source to second parallel light, and a relative distance between the first light source and the first collimator and a relative distance between the second light source and the second collimator are adjusted as desired, such that a light beam diameter of the first parallel light and a light beam diameter of the second parallel light become identical to each other.

12. The light source module according to claim 7, wherein the coupler is configured to couple the first light and the second light such that a light distribution angle of the first light and a light distribution angle of the second light agree with each other.

13. The light source module according to claim 12, further including a light source-side light focusing member configured to focus the light, which is coupled by the coupler, toward the light source-side connection hole.

14. The light source module according to claim 1, further including a determination circuit configured to determine the irradiation module which is connected to the light source module, and a light source controller configured to control at least one of the first light source and the second light source, based on a determination result of the determination circuit.

15. An endoscope light source system comprising;
the source module according to claim 1, and
one of the first irradiation module or the second irradiation module, which is mechanically detachably attached to the light source module,
wherein the endoscope light source system is configured such that illumination light corresponding to a purpose of use is emitted by a combination of the light source module and the one of first irradiation module or the second irradiation module, which is mechanically detachably attached to the light source module.

16. The endoscope light source system to claim 15, wherein the first light guide member includes a bundle fiber which is formed by bundling a plurality of optical fiber strands, and the second light guide member includes a single optical fiber, such that an effective cross-sectional area of the second light guide member becomes less than a light-guide cross-sectional area of the first light guide member.

17. The endoscope light source system according to claim 16, wherein the first irradiation module includes an intensity uniformizing member configured to uniformize a light intensity in a cross section of the light in a direction perpendicular to an optical axis of the light which is incident on the first irradiation-side connector and to make the light having a light intensity uniformized be incident on the bundle fiber;

wherein the second irradiation module includes an irradiation-side light focusing member which focuses the light to the single optical fiber, which the light incident on the first irradiation-side connector, and to make the light be incident on the single optical fiber, wherein the intensity uniformizing member is one of a rod lens or a GRIN lens, and the irradiation-side light focusing member is one of a lens or a GRIN lens.

18. The endoscope light source system according to claim 17, wherein the light source module includes a light source-side light focusing member configured to focus the first light or the second light toward the light source-side connection hole, and wherein the light source-side light focusing member is configured to focus to the intensity uniformizing member when the first irradiation module is connected to the light source module, and is configured to focus to an end face of the second light guide member together with the irradiation-side light focusing member when the second irradiation module is connected to the light source module.

19. The endoscope light source system according to claim 15, wherein the light source module further includes;

a coupler configured to couple the first light and the second light; and a light source-side light focusing member configured to focus the light which is coupled by the coupler, toward the light source-side connection hole, and wherein in the first light guide route, the second light guide route and the third light guide route, the light source-side light focusing member does not move.

20. The endoscope light source system according to claim 15, wherein the light source module further includes;

a coupler configured to couple the first light and the second light;

a light source-side light focusing member configured to focus the light which is coupled by the coupler, toward the light source-side connection hole, and an adjusting member configured to adjust, in accordance with at least one of the light guide route and the irradiation module, at least one of a light distribution angle, an intensity distribution and a light beam diameter of the light which is incident on the irradiation-side connector from the light source module.

21. The endoscope light source system according to claim 20, wherein the adjusting member is configured to move the light source-side light focusing member in accordance with the irradiation module.

22. The endoscope light source system according to claim 15, wherein a position of the first irradiation-side connector in the first irradiation module is identical to a position of the second irradiation-side connector in the second irradiation module.

* * * * *